(12) United States Patent
Sarvetnick et al.

(10) Patent No.: US 6,753,153 B2
(45) Date of Patent: Jun. 22, 2004

(54) MARKERS FOR IDENTIFICATION AND ISOLATION OF PANCREATIC ISLET α AND β PROGENITORS

(75) Inventors: Nora Sarvetnick, San Diego, CA (US); Marcie Kritzik, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/736,911

(22) Filed: Dec. 13, 2000

(65) Prior Publication Data

US 2002/0106703 A1 Aug. 8, 2002

Related U.S. Application Data

(60) Provisional application No. 60/170,474, filed on Dec. 13, 1999.

(51) Int. Cl.[7] .................. G01N 33/53; G01N 33/543
(52) U.S. Cl. .................. 435/7.21; 435/2; 435/4; 435/7.23; 435/7.24; 435/7.25; 435/371; 435/373; 435/377; 435/378; 435/325; 436/63; 436/64; 436/172; 436/177; 436/519; 436/546; 436/548
(58) Field of Search .................. 435/2, 4, 7.21, 435/7.23, 7.24, 7.25, 371, 377, 373, 378, 325; 436/519, 546, 548, 63, 64, 172, 177

(56) References Cited

U.S. PATENT DOCUMENTS 6,242,666 B1 * 6/2001 Sarvetnick et al. ........... 800/18
6,326,201 B1 * 12/2001 Fung et al. .................. 435/325

OTHER PUBLICATIONS

Kritzik et al. (2000), "Expression of ErbB Receptors During Pancreatic Islet Development and Regrowth." *Journal of Endocrinology*, vol. 165:67–77.
Kritzik et al. (1999), "PDX–1 and Msx–2 Expression in the Regenerating and Developing Pancreas." *Journal of Endocrinology*, vol. 163:523–530.
American Type Culture Collection (1988) p. 173, especially third entry.
Pavelic et al. (1996), "Molecular Genetics of Malignant Insulinoma." *Anticancer Research*, vol. 16:1707–1718.
Graber et al. (1999), "ErbB–4 mRNA Expression is Decreased in Non–Metastatic Pancreatic Cancer." *Int. J. Cancer*, vol. 84:24–27.
Ohlsson et al. (1993), "IPF1, a Homeodomain–Containing Transactivator of the Insulin Gene." *EMBO Journal*, vol. 12(11):4251–4259.
Davidson et al. (1995) "The function and evolution of Msx genes: pointers and paradoxes." *TIG*, vol. 11(10):405–411.
Dugan et al. (1997) "HER–2/neu Expression in Pancreatic Adenocarcinoma: Relation to Tumor Differentiation and Survival." *Pancreas*, vol. 14(3):229–236.
Gu et al (1993) Epithelial cell proliferation and islet neogenesis in IFN-g transgenic mice. *Development*, vol. 118:33–46.
Hall et al. (1990) "The c–erb B–2 Proto–Oncogene in Human Pancreatic Cancer." *Journal of Pathology*, vol. 161:195–200.
LeBras et al. (1998) "A search for tyrosine kinase receptors expressed in the rat embryonic pancreas." *Diabetologia*, vol. 41:1474–1481.
Maas et al. (1996) "The Role of Msx Genes in Mammalian Development." *Ann. NY Acad. Sci.*, vol. 785:171–181.
Oberg–Welsh et al. (1996) "Effects of Certain Growth Factors on In Vitro Maturation of Rat Fetal Islet–like Structures." *Pancreas*, vol. 12(4):334–339.
Press et al. (1990) "Expression of the HER–2/neu proto–oncogene in normal human adult and fetal tissues." *Oncogene*, vol. 5:953–962.
Sander et al. (1997) "The β cell transcription factors and development of the pancreas." *J. Mol. Med.*, vol. 75:327–340.
Sundaresan et al. (1998) "Biological Response to ErbB Ligands in Nontransformed Cell Lines Correlates with a Specific Pattern of Receptor Expression." *Endocrinology*, vol. 139(12):4756–4764.

* cited by examiner

*Primary Examiner*—Long V. Le
*Assistant Examiner*—Kartic Padmanabhan
(74) *Attorney, Agent, or Firm*—Pamela J. Sherwood; Bozicevic, Field, & Francis LLP

(57) ABSTRACT

The differential expression of marker proteins in a targeted population provides a means of identifying and isolating cells. A population of cells associated with the regeneration of pancreatic islets is shown to express certain proteins, including the cell surface proteins ErbB2, ErbB3, and ErbB4; and the nuclear protein Msx-2. Populations of isolated pancreatic islet progenitor cells find use in screening assays, to characterize genes involved in islet development and regulation, and in transplantation to provide a recipient with pancreatic islet functions.

27 Claims, 7 Drawing Sheets

MARKERS FOR IDENTIFICATION AND ISOLATION OF PANCREATIC ISLET α AND β PROGENITORS

This application claims priority to provisional application Ser. No. 60/170,474 filed Dec. 13, 1999.

BACKGROUND

There are 15.7 million people in the United States who have diabetes, which is the seventh leading cause of death in this country. As a chronic disease that has no cure, diabetes is one of the most costly health problems in America. Health care and other costs directly related to diabetes treatment, as well as the costs of lost productivity, run $92 billion annually.

Type I autoimmune diabetes results from the destruction of insulin producing beta cells in the pancreatic islets of Langerhans. The adult pancreas has very limited regenerative potential, and so these islets are not replaced after they are destroyed. The patient's survival then depends on exogenous administration of insulin. There are an estimated 500,000 to 1 million people with type 1 diabetes in the United States today. The risk of developing type 1 diabetes is higher than virtually all other severe chronic diseases of childhood.

The optimal treatment of insulin-dependent diabetes mellitus (IDDM), is the regulated delivery of insulin by functional beta cells. Pancreas transplantation, however, is a major surgical procedure with a high rate of complications. Transplantation of the isolated insulin-secreting islets of Langerhans is an alternative approach, which is easier and safer than whole organ transplantation. Clinical trials of islet transplantation have begun in a few specialized centers worldwide. Insulin independence at 1 year was achieved in 8% of the patients, but 20% of cases showed a graft function with a normal basal C peptide and improved glycemic regulation.

Beta-cell transplantation has so far been restricted by the scarcity of human islet donors. This shortage could be alleviated by methods for the isolation and/or culture of beta-cell progenitors. Such cells might also be protected from immunological rejection and recurring autoimmunity by genetic manipulation. The combination of these approaches with immunoisolation devices holds the promise of a widely available cell therapy for treatment of IDDM in the near future.

The pancreas is composed of at least three types of differentiated tissue: the hormone-producing cells in islets (4 different cell types), the exocrine zymogen-containing acini, and the centroacinar cells, ductules and ducts (ductal tree). All of these cells appear to have a common origin during embryogenesis in the form of duct-like protodifferentiated cells. Later in life, the acinar and ductal cells retain a significant proliferative capacity that can ensure cell renewal and growth, whereas the islet cells become mitotically inactive.

During embryonic development, and probably later in life, pancreatic islets of Langerhans originate from differentiating epithelial stem cells. These stem cells are situated in the pancreatic ducts but are otherwise poorly characterized. Pancreatic islets contain four islet cell types: alpha, beta, delta and pancreatic polypeptide cells that synthesize glucagon, insulin, somatostatin and pancreatic polypeptide, respectively. The early progenitor cells to the pancreatic islets are multipotential and coactivate all the islet-specific genes from the time they first appear. As development proceeds, expression of islet-specific hormones becomes restricted to the pattern of expression characteristic of mature islet cells.

The characterization of pre-islet cells is of great interest for the development of therapeutics to treat diseases of the pancreas, particularly IDDM. Model systems have been described that permit the study of these cells. For example, Gu and Sarvetnick (1993) *Development* 118:33–46 identify a model system for the study of pancreatic islet development and regeneration. Transgenic mice carrying the mouse γ-interferon gene linked to the human insulin promoter exhibit inflammatory-induced islet loss. Significant duct cell proliferation occurs in these mice, leading to a striking expansion of pancreatic ducts. Endocrine progenitor cells are localized in these ducts. This model provides a source of progenitor cells for further study.

The human epidermal growth factor receptor (HER or ErbB) family consists of four distinct members, including the epidermal growth factor (EGF) receptor (EGFR, HER1, or ErbB1), ErbB2 (HER2 or neu), ErbB3 (HER3), and ErbB4 (HER4). Activation of these receptors plays an important role in the regulation of cell proliferation, differentiation, and survival in several different tissues. Binding of a specific ligand to one of the ErbB receptors triggers the formation of specific receptor homo- and heterodimers, with ErbB2 being the preferred signaling partner. The ErbB receptor ligands represent a complex variety of molecules. The EGF receptor binds six known ligands, including EGF, TGFα, heparin-binding EGF-like growth factor, amphiregulin, epiregulin and betacellulin. Other members of the ErbB receptor family appear to function primarily through interaction with the neuregulins, a family of EGF-like growth factors encoded by at least three different genes: NRG1 (NDF, heregulin, GGF, ARIA or SMDF), NRG2, NRG3 and NRG4. Alternative transcript splicing from the NRG1 and NRG2 genes results in the production of multiple neuregulin isoforms. Distinct isoforms can elicit distinct biological activities depending on the cellular context, thereby modulating growth and development independently.

The differential expression of genes by progenitor cells, as compared to their differentiated progeny, is of interest for the characterization and isolation of the progenitor cells. Where the differentially expressed genes encode a receptor for biologically active molecules, the marker may further provide information about factors that affect the growth or differentiation of the progenitor cells. Where such genes encode proteins such as transcription factors, the marker may provide information about regulated gene expression in the progenitor cells.

Relevant Literature

The expression of ErbB2 in rat embryonic pancreas has been reported by LeBras et al. (1998) *Diabetologia* 41:1474–1481. Press et al. (1990) *Oncogene* 5:953–962 found that ErbB2 was not significantly expressed in the adult pancreas, though weak staining was seen in the ducts. Sundaresan et al. (1998) *Endocrinology* 139:4756–4764 have also reported expression of ErbB receptor and ligand in a ductal epithelial cell derived from rat embryos.

Hall et al. (1990) *J Pathol* 161(3):195-200; and Dugan et al. (1997) *Pancreas* 14(3):229–36 investigate the expression of ErbB2 in pancreatic cancers. The receptor has been found to be amplified and overexpressed in a number of human adenocarcinomas. The data suggest that there is abnormal expression of c-erb B-2 oncogene in about 20 per cent of cases, although mutational activation was not seen in human pancreatic adenocarcinoma.

Oberg-Welsh and Welsh (1996) *Pancreas* 12:334–339 studied the expression of protein tyrosine kinases in different preparations of insulin producing cells by polymerase chain reaction (PCR). Among the tyrosine kinases thus identified were the fibroblast growth factor receptor-4 (FGFR-4), c-kit, the insulin-like growth factor (IGF-I) receptor, and the cytoplasmic tyrosine kinase Jak2, which associates with the activated receptor for growth hormone (GH). Fetal islet-like structures were cultured in the absence or presence of the ligands to these receptors.

Transcription factors important for insulin gene expression are critical for development of the pancreas during embryogenesis (see Sander and German (1997) *J. Mol. Med.* 75:327–340). PDX-1 is one important marker. Like PDX-1, MSX-2 is a homeobox-containing transcription factor. It is part of a conserved family of transcription factors that play critical roles in tissue patterning and organogenesis during development. Msx-2 is expressed at a wide variety of sites in the developing embryo, but no specific role is known for pancreatic development (see Davidson (1995) *Trends Genet.* 11:405–411). It is not expressed in the normal adult pancreas (Maas et al. (1996) *Ann. NY Acad. Sci.* 785:171–181).

SUMMARY OF THE INVENTION

Polypeptide markers are provided that are expressed by progenitors of pancreatic islet cells. During regeneration of pancreatic islets, receptors of the ErbB family are expressed, including ErbB2, ErbB3 and ErbB4. Transcriptional factors are also shown to be expressed, including the homeobox-containing factor Msx-2. These markers are useful in identifying progenitor cells in the lineage that produces pancreatic islet cells; and can also be used in the detection of pancreatic islet regeneration. The progeny islet cells include insulin producing beta cells, and glucagon producing alpha cells.

Those markers that are expressed on the cell surface are useful for the enrichment of islet progenitor cells from complex cell mixtures. Such progenitor populations are useful in transplantation, for experimental evaluation, and as a source of lineage and cell specific products, including mRNA species useful in identifying genes specifically expressed in these cells, and as targets for the discovery of factors or molecules that can affect them. Cultures of such cells may utilize ligands that specifically interact with the cell surface markers. Ligands of interest include the neuregulins: NRG1, NRG2 and NRG3.

DESCRIPTION OF THE SPECIFIC EMBODIMENTS

Figure 1:
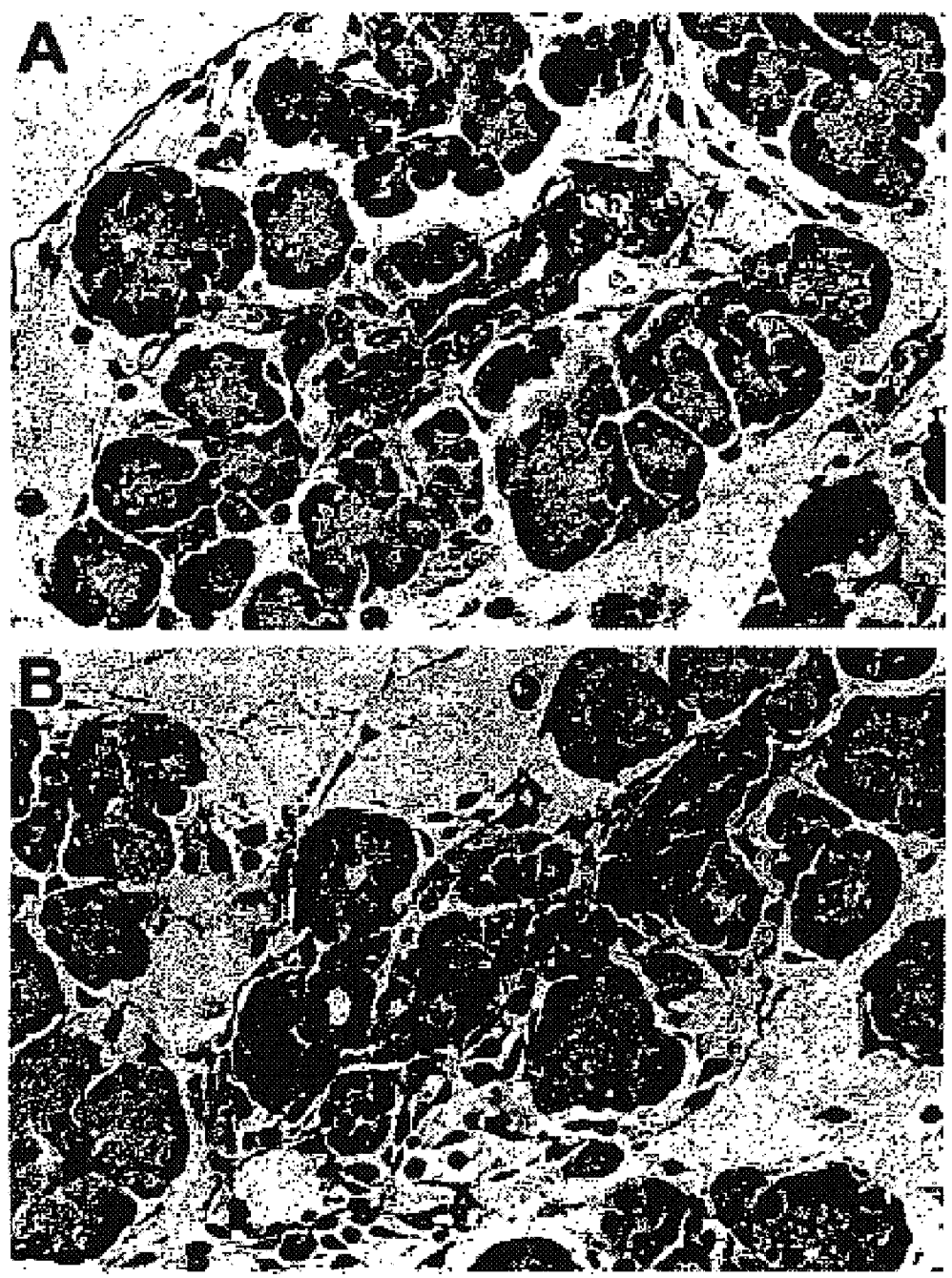
FIGS. 1A–B. ErbB2 and insulin immunostaining of the fetal pancreas. Pancreatic sections of an E14.5 embryo were immunostained with antibody to either ErbB2 (A) or insulin (B) using the ABC technique (brown is positive staining). Gill's hematoxylin was the counterstain. ErbB2 is expressed in both the ductal and peri-ductal regions, while insulin is found mainly in the periductal region. Original magnifications, 50×.

A population of cells associated with the regeneration of pancreatic islets is shown to express certain proteins, including the cell surface proteins ErbB2, ErbB3, and ErbB4; and the nuclear protein Msx-2. The differential expression of these proteins in a progenitor cell population, as compared to the surrounding tissues, provides a means of identifying and isolating cells that give rise to pancreatic islet cells, including pancreatic alpha cells and pancreatic beta cells.

The progenitor cell population is useful in transplantation to provide a recipient with pancreatic islet cells, which may produce insulin or glucagon; for drug screening; experimental models of islet differentiation and interaction with other cell types; in vitro screening assays to define growth and differentiation factors, and to additionally characterize genes involved in islet development and regulation; and the like. The native cells may be used for these purposes, or they may be genetically modified to provide altered capabilities.

Before the present invention is described, it is to be understood that this invention is not limited to the particular embodiments described, as such methods, devices, and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise, and includes reference to equivalent steps and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the specific methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Markers, as used herein, are nucleic acid or polypeptide molecules that are differentially expressed in a cell of interest. In this context, differential expression means an increased level of the marker for a positive marker, and a decreased level for a negative marker. The detectable level of the marker nucleic acid or protein is sufficiently higher or lower in the cells of interest, compared to other cells, that the cells of interest can be identified, using any of a variety of methods as known in the art.

It will be understood by those of skill in the art that differential expression is a relative term, and will vary with the amount of background expression from other cell types. It is also understood that a marker need not be specifically expressed by a cell of interest when compared to the body as a whole, as long as there is specificity within a tissue, organ, or developmental stage. For example, a protein may be found on a specific cell type within one organ, but could be widely expressed in other organs, or at different stages of development. A progenitor cell may differentially express a polypeptide that is not found in the fully differentiated progeny cell. A cell of interest may differentially express a polypeptide that is not expressed in surrounding tissues, e.g. the subject islet progenitor cells express polypeptides not found in the normal ductal epithelial cells. This specificity within an organ is sufficient for purposes of cell identification and separation.

Some markers of interest in the present invention include members of the ErbB family. These molecules, including the polypeptides and encoding nucleic acids, are well known in the art, and reagents for the detection thereof are widely available. The polypeptide and nucleic acid sequence of ErbB2 may be accessed at Genbank, accession number 004448; ErbB3 at accession number 001982; and ErbB4 at accession number L07868. Antibodies specific for these polypeptides are commercially available, or may be produced using conventional methods as known in the art.

Another marker of interest is Msx-2, a homeodomain containing protein. The polypeptide and genetic sequence of Msx-2 may be accessed at Genbank at accession number D31771, and the protein sequence at accession number BAA06549. See, for example, Jabs et al. (1993) *Cell* 75:443–450.

Pancreatic Cells: Pancreatic tissues, which may be selected from different developmental stages and sources, are of interest in the subject invention as a source of islet progenitor cells, and to supply samples for the further characterization of the islet development and regeneration process. Depending on the purpose, whole pancreas may be used, or discrete tissues derived therefrom. Of particular interest as a source of progenitor cells is pancreatic ductal tissue, which can be isolated from other pancreatic tissues by those of skill in the art.

The subject islet progenitor cells may be isolated from pancreatic ducts, which may be fetal, neonatal, juvenile or adult. However, the frequency of progenitor cells is substantially lower in tissues taken from a host older than a neonate. The progenitor cells may be obtained from any mammalian species, e.g. equine, bovine, porcine, canine, feline, rodent, e.g. mice, rats, hamster, primate, etc., particularly human. The tissue may be obtained by biopsy from a live donor, or obtained from a dead or dying donor within about 48 hours of death, or freshly frozen tissue, tissue frozen within about 12 hours of death and maintained at below about $-20°$ C., usually at about liquid nitrogen temperature ($-180°$ C.) indefinitely.

A tissue source of interest for investigative purposes is the transgenic mouse described by Gu and Sarvetnick (1993) *Development* 118:33–46. In such mice, the gene encoding interferon $\gamma$ is under the transcriptional control of the insulin promoter, and therefore is specifically expressed in the pancreas. In adult life, these animals exhibit significant duct cell proliferation and islet formation.

Marker Specific reagent: In a typical assay or separation, a cell sample is contacted with a marker-specific reagent, and detecting directly or indirectly the presence of the complex formed. The term "specific reagent" as used herein refers to a member of a specific binding pair, i.e. two molecules where one of the molecules through chemical or physical means specifically binds to the other molecule. The complementary members of a specific binding pair are sometimes referred to as a ligand and receptor.

In addition to antigen and antibody specific binding pairs, specific binding members include peptide-MHC antigen and T cell receptor pairs; complementary nucleotide sequences (including nucleic acid sequences used as probes and capture agents in DNA hybridization assays); peptide ligands and receptor, e.g. neuregulins and ErbB receptors; autologous monoclonal antibodies, and the like. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc. so long as an epitope is present.

Immunological specific binding pairs include antigens and antigen specific antibodies or T cell antigen receptors. Recombinant DNA methods or peptide synthesis may be used to produce chimeric, truncated, or single chain analogs of either member of the binding pair, where chimeric proteins may provide mixture(s) or fragment(s) thereof, or a mixture of an antibody and other specific binding members. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding reagents are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent analysis or sorting for each marker.

Monoclonal antibodies specific for the subject markers may be produced in accordance with conventional ways, immunization of a mammalian host, e.g. mouse, rat, guinea pig, cat, dog, etc., fusion of resulting splenocytes with a fusion partner for immortalization and screening for antibodies having the desired affinity to provide monoclonal antibodies having a particular specificity. These antibodies can be used for affinity chromatography, ELISA, RIA, and the like. The antibodies may be labeled with radioisotopes, enzymes, fluorescers, chemiluminescers, or other label which will allow for detection of complex formation between the labeled antibody and its complementary epitope.

Nucleic acid sequences for detection may be complementary to the coding or non-coding sequences of the corresponding genes. Complementary nucleic acids may be cDNA, mRNA or genomic DNA, or a fragment thereof. Fragments may be obtained of the DNA sequence by chemically synthesizing oligonucleotides in accordance with conventional methods, by restriction enzyme digestion, by PCR amplification, etc. For the most part, DNA fragments will be of at least 25 nt, usually at least 30 nt, more usually at least about 50 nt. Such small DNA fragments are useful as primers for PCR, hybridization screening, etc. Where it is desirable to generate probes or primers that distinguish Msx-2, or an ErbB receptor from related family members, the probe may be derived from the less conserved region of the genes.

For hybridization probes, it may be desirable to use nucleic acid analogs, in order to improve the stability and binding affinity. The term "nucleic acid" shall be understood to encompass such analogs. A number of modifications have been described that alter the chemistry of the phosphodiester backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2☐-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Detection of Expression of Markers on Islet Progenitor Cells

The data provided herein demonstrates that proteins of the ErbB receptor family, specifically ErbB2, ErbB3 and ErbB4 are expressed by progenitor cells found in the pancreatic duct, which cells can develop into pancreatic islet cells. Of particular utility is ErbB3 as a marker for progenitor cells that go on to form islet β cells. The expression of ErbB4 is also associated with progenitor cells that form glucagon producing islet α cells. The islet progenitor cells of interest also express the transcription factor Msx-2.

Polypeptide Analysis

Screening may be based on the functional or antigenic characteristics of the protein, e.g. immunoassays, determination of Msx-2 directed transcription, response to an ErbB receptor ligand, etc.

A pancreatic cell sample, preferably a pancreatic duct sample, is taken from a suitable donor. Biopsy and autopsy samples or other sources of pancreatic tissues are of particular interest. Also included in the invention are derivatives and fractions of such cells and tissues. The number of cells in a sample will generally be at least about $10^3$, usually at least $10^4$, and may be about $10^5$ or more. The cells may be dissociated, in the case of solid tissues, or tissue sections may be analyzed. Alternatively a lysate of the cells may be prepared.

Detection may utilize staining of cells or histological sections, performed in accordance with conventional methods. Methods of cell staining may be performed as follows. The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are treated will be any medium which maintains the viability of the cells. A preferred medium is phosphate buffered saline containing from 0.1 to 0.5% BSA. Various media are commercially available and may be used according to the nature of the cells, including Dulbecco☐s Modified Eagle Medium (dMEM), Hank's Basic Salt Solution (HBSS), Dulbecco☐s phosphate buffered saline (dPBS), RPMI, Iscove☐s medium, PBS with 5 mM EDTA, etc., frequently supplemented with fetal calf serum, BSA, HSA, etc.

The antibody may be labeled for direct detection, as previously described. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including microscopy, radiography, scintillation counting, etc. The staining intensity of cells can be monitored by flow cytometry, where lasers detect the quantitative levels of fluorochrome (which is proportional to the amount of cell surface antigen bound by the antibodies). Flow cytometry, or FACS, can also be used to separate cell populations based on the intensity of antibody staining, as well as other parameters such as cell size and light scatter. Although the absolute level of staining may differ with a particular fluorochrome and antibody preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest cells in a bone marrow sample are designated as 4 logs more intense than the cells having the lowest level of staining. When displayed in this manner, it is clear that the cells falling in the highest log of staining intensity are bright, while those in the lowest intensity are negative. An alternative control may utilize a substrate having a defined density of antigen on its surface, for example a fabricated bead or cell line, which provides the positive control for intensity.

An alternative method for diagnosis depends on the in vitro detection of binding between antibodies and the subject polypeptide markers in a lysate. Measuring the concentration of marker binding in a sample or fraction thereof may be accomplished by a variety of specific assays. A conventional sandwich type assay may be used. For example, a sandwich assay may first attach marker specific antibodies to an insoluble surface or support. The particular manner of binding is not crucial so long as it is compatible with the reagents and overall methods of the invention. They may be bound to the plates covalently or non-covalently, preferably non-covalently. A sample derived from candidate pancreatic islet progenitor cells is contacted with the bound antigen, and the presence of bound complexes determined by any convenient method.

Other immunoassays are known in the art and may find use. Ouchterlony plates provide a simple determination of antibody binding. Western blots may be performed on protein gels or protein spots on filters, using a detection system specific for marker as desired, conveniently using a labeling method as described for the sandwich assay.

Other diagnostic assays of interest are based on the functional properties of marker proteins. For example, a functional assay may be based on the transcriptional changes mediated by Msx-2 gene products. Other assays may, for example, detect DNA footprinting changes due to complexes formed between Msx-2 and its binding motif. Ligands to ErbB receptors may be added to a culture of candidate progenitor cells, and the response measured.

Nucleic Acid Analysis

A number of methods are available for analyzing nucleic acids for the presence or absence of a specific sequence. For analysis based on nucleic acids, mRNA or nucleic acids derived therefrom are analyzed for the presence of marker specific sequences. mRNA in a sample may be used directly, or may be reverse transcribed to generate a cDNA strand. The cDNA may be amplified by conventional techniques, such as the polymerase chain reaction (PCR), to provide sufficient amounts for analysis. The use of the polymerase chain reaction is described in Saiki, et al. (1985) Science 239:487, and a review of techniques may be found in Sambrook, et al. Molecular Cloning: A Laboratory Manual, CSH Press 1989, pp.14.2□114.33. Amplification may also be used to determine whether a specific sequence is present, by using a primer that will specifically bind to the desired sequence, where the presence of an amplification product is indicative that a specific binding complex was formed. Alternatively, the mRNA sample is fractionated by electrophoresis, e.g. capillary or gel electrophoresis, transferred to a suitable support, e.g. nitrocellulose and then probed with a fragment of the marker sequence. Other techniques may also find use, including oligonucleotide ligation assays, binding to solid state arrays, etc. Detection of mRNA having the subject sequence is indicative of marker gene expression in the sample.

The sample nucleic acid, e.g. mRNA or amplification product, is analyzed by one of a number of methods known in the art. Hybridization with a marker specific sequence may be used to determine its presence, by in situ hybridization, northern blots, dot blots, etc. The hybridization pattern of a control and variant sequence to an array of oligonucleotide probes immobilized on a solid support, as described in U.S. Pat. No. 5,445,934, or in WO95/35505, may also be used as a means of detection. For examples of arrays, see Hacia et al. (1996) Nature Genetics 14:441–447; Lockhart et al. (1996) Nature Biotechnol. 14:1675–1680; and De Risi et al. (1996) Nature Genetics 14:457–460.

Isolation of Pancreatic Islet Progenitor Cells

Methods for enrichment of islet progenitor cell subsets are provided. The enriched cell population will usually have at least about 50% cells of the selected phenotype, more usually at least 75% cells of the selected phenotype, and may be 90% or higher of the selected phenotype. The subject cell populations are separated from other cells, e.g. differentiated islet and duct cells, on the basis of specific markers, which are identified with affinity reagents, e.g. monoclonal antibodies. Markers of interest include ErbB receptors, as previously described. The separation may also use negative markers to exclude differentiated epithelial or islet cells.

The subject subsets are separated from a complex mixture of cells by techniques that enrich for cells having the above characteristics. For isolation of cells from tissue, an appropriate solution may be used for dispersion or suspension. Such solution will generally be a balanced salt solution, e.g. normal saline, PBS, Hank□s balanced salt solution, etc., conveniently supplemented with fetal calf serum or other naturally occurring factors, in conjunction with an acceptable buffer at low concentration, generally from 5–25 mM. Convenient buffers include HEPES, phosphate buffers, lactate buffers, etc.

Separation of the subject cell populations will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, eg. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the selected cells.

The labeled cells are then separated as to the expression of one or more of the differentially expressed markers. The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, lscove□s medium, etc., frequently supplemented with fetal calf serum.

Culture of Islet Progenitor Cells

The enriched cell population may be grown in vitro under various culture conditions. Culture medium may be liquid or semi-solid, e.g. containing agar, methylcellulose, etc. The cell population may be conveniently suspended in an appropriate nutrient medium, such as DMEM:Ham's F12 or RPMI-1640, normally supplemented with fetal calf serum (about 5–10%), L-glutamine, and antibiotics, e.g. penicillin and streptomycin.

The subject progenitor cells are characterized by their expression of growth factor receptors. In addition to providing a convenient marker for separation, the cognate ligands may biologically active on the cells, and find use in the in vitro culture of the cells. The subject cells express high levels of ErbB receptors on their cell surface. The biologically relevant receptor is likely to be a heterodimer between either ErbB2/ErbB3, and/or ErbB2/ErbB4.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Specific growth factors that may be used in culturing the subject cells include heregulin, epidermal growth factor, TGFα, heparin-binding EGF-like growth factor, keratinocyte growth factor, amphiregulin, epiregulin, betacellulin, NRG2, NRG3, NRG4, and the like. The specific culture conditions are chosen to achieve a particular purpose, i.e. differentiation into insulin producing cell populations, maintenance of progenitor cell activity, etc.

The subject cells are found to grow as a monolayer. However, in some circumstances it may be desirable to include a co-culture with stromal or feeder layer cells. Stromal cells suitable for use in the growth of hematopoietic cells are known in the art. These include fibroblasts, e.g. pancreatic derived fibroblasts, STO cells (Axelrod (1984) Dev Biol 101(1):225–8; Kitani et al. (1996) Zoolog Sci 13(6):865–71); bone marrow stroma as used in "Whitlock-Witte" (Whitlock et al. [1985] *Annu Rev Immunol* 3:213–235) or "Dexter" culture conditions (Dexter et al. [1977] *J Exp Med* 145:1612–1616); and heterogeneous thymic stromal cells (Small and Weissman [1996] *Scand J Immunol* 44:115–121).

Uses of Progenitor Cells

The subject cultured cells may be used in a wide variety of ways. The nutrient medium, which is a conditioned medium, may be isolated at various stages and the components analyzed. Separation can be achieved with HPLC, reversed phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions.

The progenitor cells may be used in conjunction with the culture system in the isolation and evaluation of factors associated with the differentiation and maturation of islet cells. Thus, the progenitor cells may be used in assays to determine the activity of media, such as conditioned media, evaluate fluids for growth factor activity, involvement with dedication of lineages, or the like.

The subject islet progenitor cell populations may be used for reconstitution of islet cell function in a recipient, e.g. insulin producing beta cells, glucagon producing cells, etc. The condition may be caused by genetic or environmental conditions, e.g. autoimmune diseases, type I diabetes mellitus, etc. Autologous cells or allogeneic cells, may be used for progenitor cell isolation and subsequent transplantation.

Genes may be introduced into the progenitor cells for a variety of purposes, e.g. prevent HIV infection, replace genes having a loss of function mutation, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to transfect the target cells, e.g. electroporation, calcium precipitated DNA, fusion, transfection, lipofection and the like. The particular manner in which the DNA is introduced is not critical to the practice of the invention.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. For examples of progenitor and stem cell genetic alteration, see Svendsen et al. (1999) *Trends Neurosci*. 22(8):357–64; Krawetz et al. (1999) *Gene* 234(1):1–9; Pellegrini et al. *Med Biol Eng Comput*. 36(6):778–90; and Alison (1998) *Curr Opin Cell Biol*. 10(6):710–5.

To prove that one has genetically modified progenitor cells, various techniques may be employed. The genome of the cells may be restricted and used with or without amplification. The polymerase chain reaction; gel electrophoresis; restriction analysis; Southern, Northern, and Western blots; sequencing; or the like, may all be employed. The cells may be grown under various conditions to ensure that the cells are capable of differentiation while maintaining the ability to express the introduced DNA. Various tests in vitro and in vivo may be employed to ensure that the pluripotent capability of the cells has been maintained.

The progenitor cells may be administered in any physiologically acceptable medium, e.g. intravascularly, including intravenous, although they may also be introduced into other convenient sites, where the cells may find an appropriate site for regeneration and differentiation. Usually, at least $1 \times 10^3$ cells will be administered, more usually at least about $1 \times 10^4$, preferably $1 \times 10^6$ or more. The cells may be introduced by injection, catheter, or the like.

Support matrices in which the progenitor cells can be incorporated or embedded include matrices which are recipient-compatible and which degrade into products which are not harmful to the recipient. Natural and/or synthetic biodegradable matrices are examples of such matrices. Natural biodegradable matrices include plasma clots, e.g., derived from a mammal, and collagen matrices. Synthetic biodegradable matrices include synthetic polymers such as polyanhydrides, polyorthoesters, and polylactic acid. Other examples of synthetic polymers and methods of incorporating or embedding cells into these matrices are known in the art. See e.g., U.S. Pat. Nos. 4,298,002 and 5,308,701. These matrices provide support and protection for the progenitor cells in vivo and are, therefore, the preferred form in which the progenitor cells are introduced into the recipient subjects.

Some treatments for diabetes have utilized the transplantation of healthy pancreatic islets, usually encapsulated in a membrane to avoid immune rejection. For example, a tubular membrane can be coiled in a housing that contained islets. The membrane is connected to a polymer that in turn connects the device to blood vessels. By manipulation of the membrane permeability, so as to allow free diffusion of glucose and insulin back and forth through the membrane, yet block passage of antibodies and lymphocytes, normoglycemia can be maintained (Sullivan et al. (1991) *Science* 252:718). Alternatively, hollow fibers containing islet cells can be immobilized in a polysaccharide alginate (Lacey et al. (1991) *Science* 254:1782). Islets have also been placed in microcapsules composed of alginate or polyacrylates.

The pancreatic progenitor cells of the invention can be used for treatment of diabetes because they have the ability to differentiate into cells of pancreatic lineage, e.g., β islet cells. The progenitor cells of the invention can be cultured in vitro under conditions which can further induce these cells to differentiate into mature pancreatic cells, or they can undergo differentiation in vivo once introduced into a subject.

Many methods for encapsulating cells are known in the art. For example, insulin producing cells or progenitors thereof may be encapsulated in implantable hollow fibers. Such fibers can be pre-spun and subsequently loaded with the cells, or can be co-extruded with a polymer which acts to form a polymeric coat about the cells.

In addition to providing a source of implantable cells, either in the form of the progenitor cell population of the differentiated progeny thereof, the subject cells can be used to produce cultures of pancreatic cells for production and purification of secreted factors. For instance, cultured cells can be provided as a source of insulin.

The subject cells are useful for in vitro assays and screening to detect factors that are active on islet progenitors. A wide variety of assays may be used for this purpose, including immunoassays for protein binding; determination of cell growth, differentiation and functional activity; production of hormones; and the like.

Of particular interest is the examination of gene expression in the progenitor cells of the invention. The expressed set of genes may be compared with a variety of cells of interest, e.g. insulin producing beta cells, fetal pancreatic tissues, etc., as known in the art. For example, in order to determine the genes that are regulated during development, one could compare the set of genes expressed by duct cells to islet cells.

Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+mRNA. One of skill in the art can readily use these methods to determine differences in the size or amount of mRNA transcripts between two samples. For example, the level of particular mRNAs in progenitor cells is compared with the expression of the mRNAs in a reference sample, e.g. differentiated cells.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., *Science* (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. Nos. 5,776,683; and 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Hybridization to arrays may be performed, where the arrays can be produced according to any suitable methods known in the art. For example, methods of producing large arrays of oligonucleotides are described in U.S. Pat. Nos. 5,134,854, and 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

It is to be understood that this invention is not limited to the particular methodology, protocols, cell lines, animal species or genera, and reagents described, as such may vary.

It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

EXAMPLE 1

Expression of ErbB Receptors during Pancreatic Islet Development and Regrowth

Expression of the ErbB receptor family and one of its ligands, heregulin, were characterized in order to identify molecules associated with pancreatic development and regeneration. In addition to studying expression during fetal pancreatic development, the expression was studied during pancreatic regeneration in the IFNγ transgenic mouse, which exhibits significant duct cell proliferation and new islet formation. These studies demonstrate significant expression of the ErbB2, ErbB3, and ErbB4 receptors, as well as heregulin isoforms, in the developing fetal pancreas.

In addition, significant ductal expression of these proteins was found during IFNγ-mediated pancreatic regeneration. This striking expression was largely absent in one week old neonates but was clearly visible in pups by five weeks of age. These data therefore indicate that ErbB receptor and ligand expression decline by birth in both the IFNγ transgenic and non-transgenic mice, and that expression resumes early in postnatal life in the IFNγ transgenic mice. The expression of ErbB receptor family members at sites of islet development and regrowth suggests that these molecules are relevant to these processes.

Materials and Methods

Animal Husbandry. Animals were maintained in a specific pathogen-free facility at The Scripps Research Institute according the rules and regulations governed and enforced by the Institutional Animal Care and Use Committee. Animals were housed under a controlled 12-hour light/dark cycle and provided with food and water ad libitum.

Transgenic Mice. Transgenic mice expressing IFNγ have been described previously (Gu et al. (1993), supra.) The IFNγ transgenic mice used in these studies were on the NOD background. IFNγ mice that have been backcrossed onto the NOD/Shi strain for more than ten generations have a very low incidence of diabetes, <20% as compared to NOD mice, which exhibit an incidence of ~25% for males and ~80% for females. Embryos were harvested at defined stages of development, with the day of plug formation counted as day 0.5.

Immunohistochemistry. Pancreata harvested from mice were fixed overnight in 10% neutral buffered formalin (3.6% formaldehyde) and embedded in paraffin. 5 m paraffin sections were either conventionally stained with hematoxylin and eosin (H&E) for histological evaluation or were stained with antibodies against ErbB2, ErbB3, ErbB4, HRG or HRG 3 using immunocytochemical techniques. Briefly, sections were deparaffinized and blocked with 2% normal goat serum before applying the primary antibodies (Santa Cruz Biotechnology, Santa Cruz, Calif.: #sc-284 (ErbB2); #sc-285 (ErbB3); #sc-283 (ErbB4); #sc-348 (HRG ); #sc-347 (HRG 3)). These antibodies were raised against peptides (17–20 amino acids in length) specific for each protein. As reported by the manufacturer, the antibodies against ErbB2, ErbB3, and ErbB4 do not cross react in Western blots of murine samples. We see distinct patterns of expression with each of these antibodies in immunohistochemistry as well, further indicating the specificity of these reagents. In addition, the HRG 3 antibody does not cross react with other heregulin family members. The HRG antibody is directed against a peptide from the carboxyl terminus of the heregulin precursor. Although it is non cross-reactive with mature forms of the heregulin family and will not recognize HRG 3, other alpha and beta heregulin isoforms might be detected with this reagent. Binding of the primary antibody was detected using the appropriate secondary antibody (Vector Laboratories, Burlingame, Calif.), and the horseradish peroxidase (HRP)-labeled avidin-biotin complex (ABC kit, Vector Laboratories). Endogenous peroxidase activity was quenched with 1% hydrogen peroxide in methanol. HRP was visualized using 3,3'-diaminobenzidine as a substrate. Gill's hematoxylin was used as a counterstain.

Results

ErbB receptor and ligand expression during fetal development. To begin to assess the involvement of ErbB receptors during pancreatic development, we first sought to characterize ErbB receptor expression in the fetal pancreas during mouse development. We have previously demonstrated the presence of ErbB1 (the EGF receptor) in the apical cytoplasm of select acinii in the IFNγ transgenic pancreas. These acinii appeared to be in a state of transition, as they exhibited ductal characteristics. Most ducts in the transgenic pancreas did not express ErbB1. Therefore, we chose to concentrate our studies on the other members of the ErbB receptor family.

Figure 2:
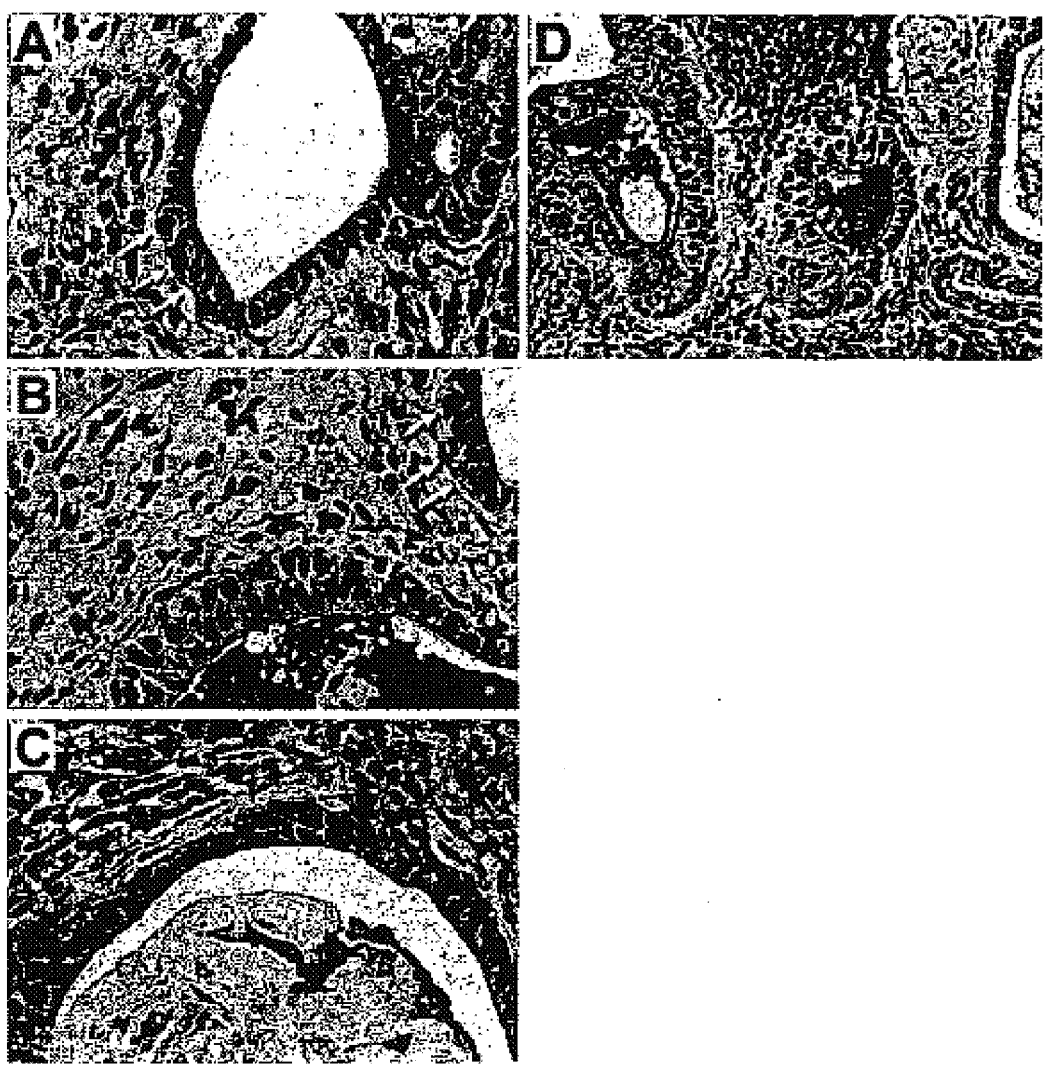
FIGS. 2A–D. ErbB receptor and ligand immunostaining of the fetal pancreas. Pancreatic sections of an E16 embryo were immunostained with antibody to either ErbB3 (A), ErbB4 (B), HRG (C), or HRG 3 (D) using the ABC technique (brown is positive staining). Gill's hematoxylin was the counterstain. Significant expression of ErbB receptors and ligands is seen in the fetal pancreatic ducts. Original magnifications, 40×.

To this end, fetal sections taken from non-transgenic mice were analyzed for expression of the ErbB2, ErbB3, and ErbB4 receptors. As indicated in FIG. 1A, we observed significant expression of ErbB2 in the primitive ducts of the fetal pancreas at E14.5 (FIG. 1A). We also observed some staining in cells within acinar structures. In comparison with ErbB2 receptor staining patterns, FIG. 1B illustrates the pattern of insulin staining in the E14.5 fetal pancreas. As illustrated in this Figure, most of the insulin stain is localized to the periphery of the fetal ducts. As with ErbB2 staining, ErbB3 and Erb4 were also expressed in the fetal ducts during pancreatic development (FIGS. 2A and 2B).

Given the expression of the ErbB receptors in the fetal pancreas, we anticipated that ErbB receptor ligands would also be present in this region. The expression of heregulin isoforms was also assessed. These analyses demonstrated significant immunoreactivity with both the HRG and HRG 3 antibodies in the fetal ducts, indicating the presence of heregulin isoforms during fetal pancreatic development (FIGS. 2C and 2D). The demonstration of significant ErbB receptor and ligand expression in the primitive ducts of the fetal pancreas is striking and, given the ductal derivation of endocrine cells during pancreatic development, it suggests that this receptor family is important for pancreatic islet development during ontogeny.

Figure 3:
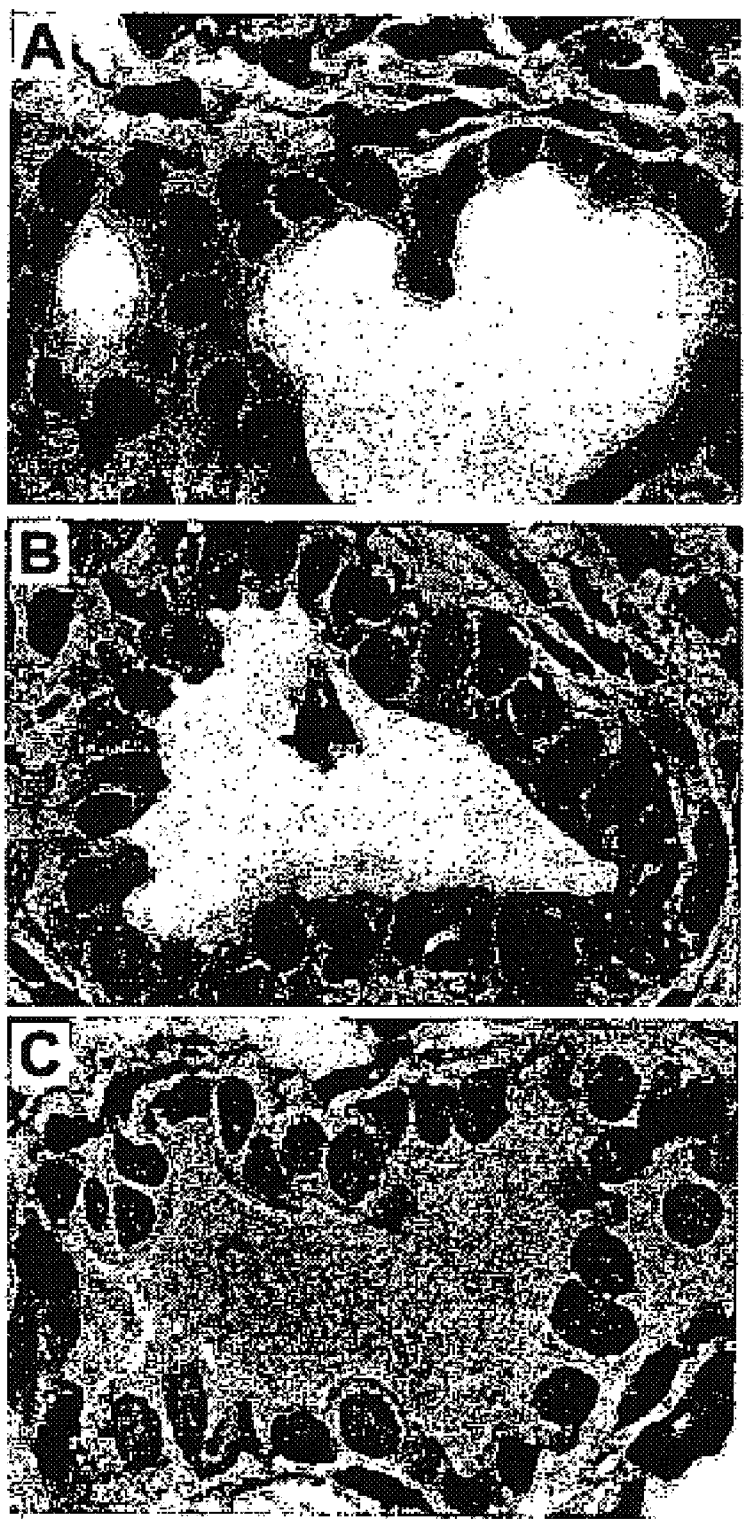
FIGS. 3A–C. ErbB receptor and ligand immunostaining of the IFNγ transgenic pancreas. Pancreatic sections from adult IFNγ transgenic mice were immunostained with antibody to either ErbB2 (A), ErbB3 (B), ErbB4 (C), HRG (brown is positive staining). Gill's hematoxylin was the counterstain. Note the expression of ErbB receptors and ligands in the pancreatic ducts. Significant ErbB receptor and ligand expression is not observed in non-transgenic mice. Original magnifications, 80×.

ErbB receptor expression in pancreatic ducts of the IFNg Transgenic Pancreas. immunohistochemistry was used to define ErbB receptor expression patterns during regeneration in the pancreatic ducts of the IFNγ transgenic mouse. FIGS. 3A, 3B, and 3C illustrate ErbB2, ErbB3, and ErbB4 receptor staining in the IFNγ transgenic pancreas, respectively. Significantly, we observed substantial expression of ErbB receptors in duct cells of the regenerating pancreas. The extent and proportion of ErbB receptor-expressing cells varied among ducts, with some ducts containing few, if any, ErbB positive cells, while other ducts contained many ErbB positive cells. In general, ErbB2 staining was much more widespread than ErbB3 or ErbB4 staining. Although the intense ErbB receptor expression patterns observed in ducts of the IFNγ transgenic pancreas were not observed in the non-transgenic pancreas, we did observe very occasional weak ErbB receptor expression in the ducts of non-transgenic mice. We also stained the regenerating pancreas for expression of heregulin isoforms. We observed significant duct cell-specific expression using both the HRG and HRG 3 antibodies in the transgenic pancreas as well. The acinar tissue did not stain with any of the heregulin ligand or receptor antibodies used.

ErbB receptor and ligand expression in pancreatic ducts during postnatal pancreatic development. The expression of ErbB receptors in the fetal pancreas as well as in the IFNγ transgenic pancreas is in contrast to our observations in the adult non-transgenic pancreas. These findings suggested that either ErbB receptor expression was maintained in the transgenic pancreas from early in development through adulthood, or that it declined as in the non-transgenic fetal pancreas, only to be induced postnatally. These distinct possibilities prompted us to examine the pattern of ErbB receptor expression in the IFNγ transgenic and non-transgenic pancreas early in postnatal life.

Figure 4:
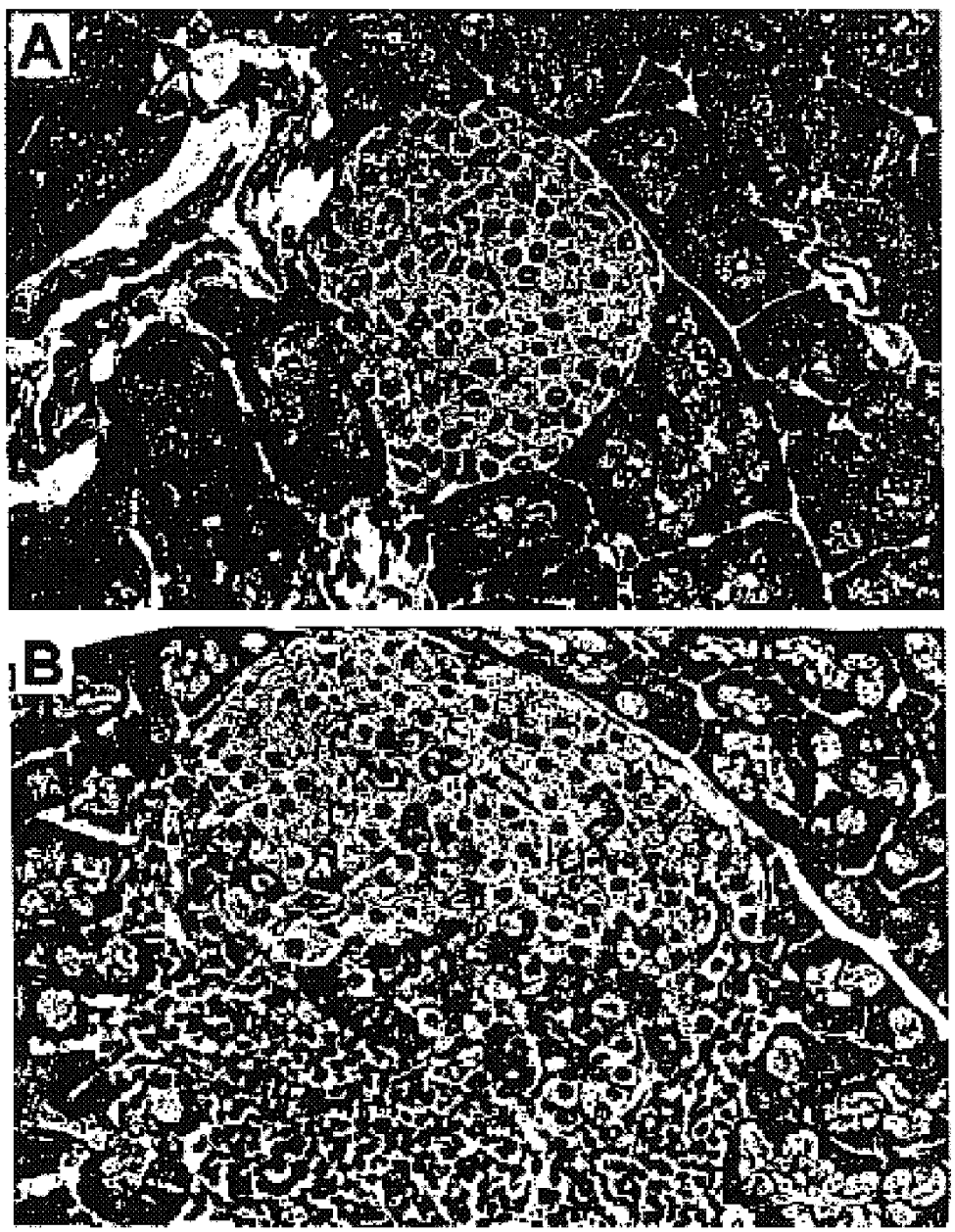
FIGS. 4A–B. Postnatal expression of ErbB2 in the IFNγ transgenic pancreas. Pancreatic sections from one week (A) or five week (B) IFNγ transgenic pups were immunostained with antibody to ErbB2 using the ABC technique (brown is positive staining). Gill's hematoxylin was the counterstain. There is an absence of ErbB2 ductal staining in the one week old pup, and presence of significant ErbB2 immunoreactivity in the five week old pup. Significant ductal expression of ErbB2 was not observed in non-transgenic pups at either age. Original magnifications, 80× (A); 64× (B).

We stained pancreatic sections taken from IFNγ transgenic and non-transgenic mice soon after birth, at one week of age, with the ErbB2, ErbB3, ErbB4, HRG, and HRG 3 antibodies. Interestingly, we did not detect significant staining in the ducts of the transgenic or non-transgenic mice with any of the antibodies screened (FIG. 4A). We next examined expression a few weeks later, at five weeks of age, in order to determine if expression had recommenced in the transgenic mice at this point. At this age, we were already able to observe expansion of pancreatic ducts in the transgenic mice as compared to the non-transgenic mice. Indeed, by this time, we did observe significant ductal staining using the ErbB receptor and ligand antibodies in the IFNγ transgenic mice, but not in the non-transgenic mice (FIG. 4B). These data therefore indicate that while ErbB receptor and ligand expression decline significantly by birth in both IFNγ transgenic and non-transgenic mice, expression resumes in the transgenic mice relatively early in postnatal life.

Figure 5:
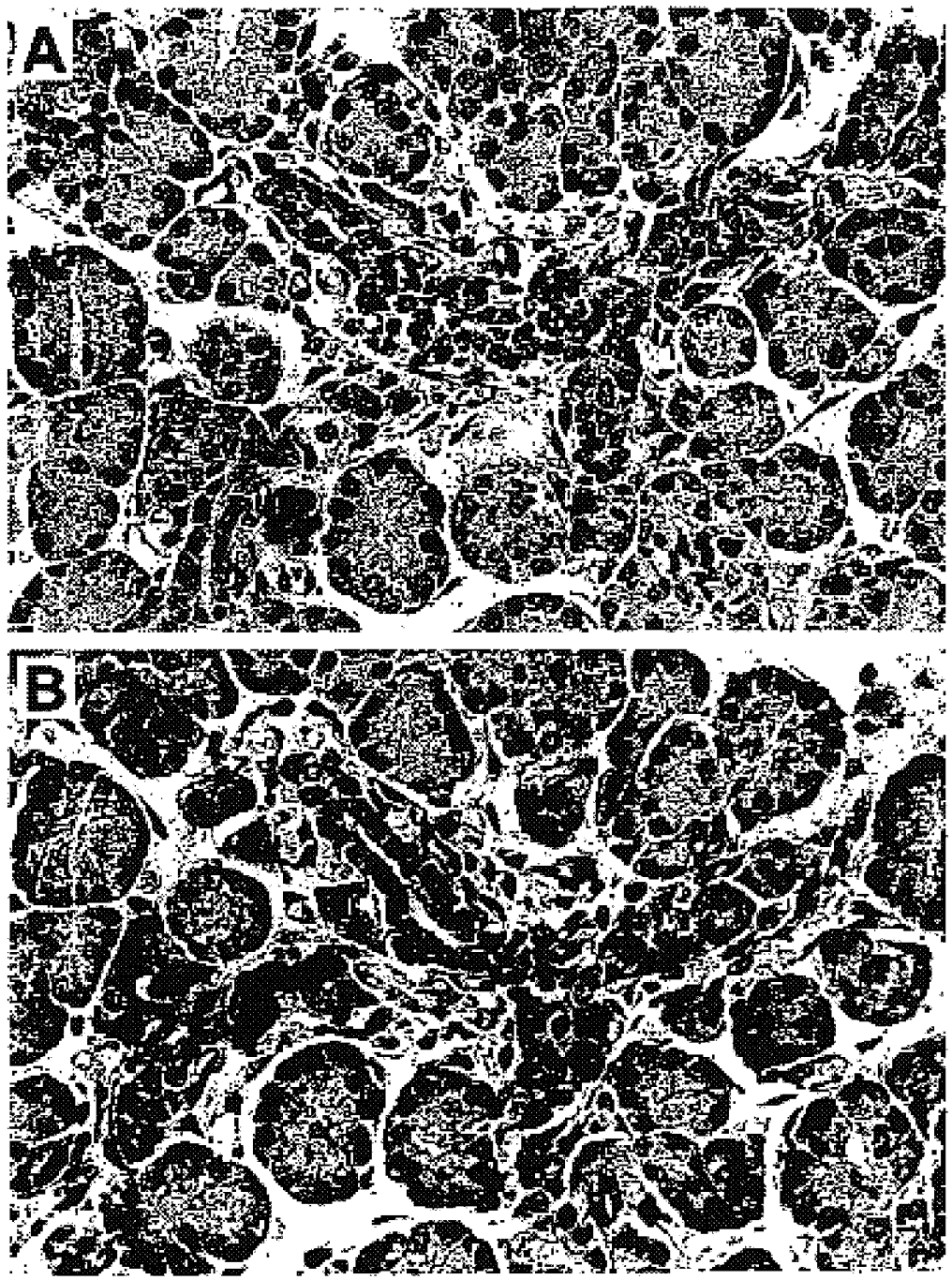
FIGS. 5A–B. Msx and insulin staining of the fetal pancreas. Serial sections of an E14.5 embryo were stained with antibody to either Msx (A) or insulin (B). Magnification 50×.

ErbB receptor expression in pancreatic islets. We observed a striking induction of intra-islet ErbB2 expression in islets that exhibited infiltration by inflammatory cells, compared to non-infiltrated islets (FIGS. 5A and 5B). Within the same field, we observed islets exhibiting different degrees of ErbB2 induction, with the degree of expression correlated with the extent of lymphocytic infiltration of the islet. Indeed, the enhanced ErbB2 islet staining was found to be adjacent to the infiltrates. This striking pattern of staining was not observed in the absence of islet infiltration, as in NOD.SCID mice. ErbB4 receptor staining also exhibited a distinct pattern of expression above the basal level of staining previously described. That is, elevated ErbB4 expression was predominantly localized at the periphery of the islets, in a pattern reminiscent of glucagon-secreting A cell organization (FIGS. 5C and 5D). This pattern of expression is distinct from insulin staining patterns. In contrast, islet staining with the ErbB3 antibody did not exhibit such striking patterns of expression.

The ErbB receptor family members are expressed at a wide variety of sites during development, including the fetal pancreas. In these studies, we have examined the expression of this receptor family during fetal pancreatic development, where we have observed defined expression of ErbB receptors in the primitive fetal ducts, from which endocrine cells and hence new islets develop. In addition, we have explored receptor expression in the IFNγ transgenic mouse, which exhibits striking duct cell proliferation and new islet formation throughout adulthood. The expression of ErbB receptor family members during new islet formation in the IFNγ transgenic mouse, as well as in islet development during ontogeny, suggests a role for these molecules in the development and regrowth of pancreatic islets.

The ductal derivation of endocrine cells during fetal islet development has been well described, and it has been previously shown that endocrine cells derive from duct cells in the IFNγ transgenic pancreas (Gu et al. (1994) supra.) These data suggest that endocrine progenitor cells exist within the pancreatic ducts and can initiate new islet growth under the appropriate conditions. Given their expression during islet growth in development (in the fetal pancreas) and regeneration (in the IFNγ transgenic pancreas), our data further suggest that the ErbB receptors are associated with endocrine progenitor cells within the duct wall.

Whereas ducts in the IFNγ transgenic pancreas exhibited significant expression of the ErbB receptors and the neuregulins, those in the non-transgenic NOD pancreas did not. This is in contrast to studies of the fetal pancreas during development. Upon examination of ErbB receptor and ligand staining patterns during pancreatic development, considerable staining was seen in the fetal ducts of non-transgenic embryos. In addition, ductal expression of these receptors diminishes by one week of age, although it is resumed in the pancreatic ducts after a few weeks of life in the IFNγ transgenic mice.

Considerable evidence exists which suggests that the formation of receptor heterodimers between members of the ErbB receptor family play an important role in mediating signaling events. Indeed, although nearly all receptor combinations are able to form, ErbB2 appears to be the preferred heterodimerization partner for the other ErbB receptors. In addition, receptor complexes with ErbB2 appear to have the highest affinity for ligand and are the most active complexes. However, none of the ligands described so far appears to bind ErbB2 directly. Rather, a variety of studies have shown that several ligands, including EGF, neuregulins, and betacellulin, are able to mediate the phosphorylation and activation of ErbB2, via heterodimerization with ErbB1, ErbB3, or ErbB4. Recent work has demonstrated that the ability of cells to respond to a given ligand is dependent on the expression of specific ErbB receptor combinations in the target tissue. In addition, Jones et al. have recently documented extreme variations in ligand binding specificities and affinities observed with different ErbB receptor dimer combinations (Jones et al. (1999) *FEBS* 447 227–231). Thus diversity in signaling events involving ErbB receptors is generated by a number of critical factors, including ligand isoforms, receptor dimer composition, and the restricted expression of receptors during development and in adulthood.

The expression of ErbB2, ErbB3, and ErbB4 receptors in the IFNγ transgenic pancreas suggests that multiple combinations of receptor heterodimers are able to form, enabling interaction with a wide range of ligands and generating diversity in signaling events. The detection of heregulin family members at times of ErbB receptor expression suggests that these molecules, which have a high affinity for the ErbB2/3 and ErbB2/4 receptor heterodimers, are likewise involved in ErbB receptor-mediated events.

We observed mainly membrane-associated and cytoplasmic staining of the ErbB receptors. In addition, we have also observed some expression over the nuclear region in the fetal as well as in the IFNγ transgenic pancreas. This was particularly evident for ErbB3, ErbB4, and HRG in the acinar and ductal regions of the fetal pancreas. Furthermore, the occasional duct staining that was observed in the non-transgenic pancreas with the ErbB2, ErbB3, and ErbB4 antibodies was often over the nuclear region; no cytoplasmic or membrane-associated ErbB receptor staining was detected in these samples.

There was a significant enhancement of ErbB2 expression in islets that correlated with the extent of lymphocytic infiltration of the islet. This increase in the expression of ErbB2 was striking, as intact islets adjacent to infiltrated islets in the same section did not display such increased expression of ErbB2. Interestingly, ErbB4 gave a distinct pattern of islet expression as well. In this case, the peripherally localized expression of ErbB4 in the pancreatic islets was reminiscent of that seen for the glucagon-expressing A cells, and it suggests that ErbB4 might participate directly in the differentiation and/or maintenance of this endocrine cell type.

In summary, the above results demonstrate significant expression of the ErbB2, ErbB3, and ErbB4 receptor tyrosine kinases, as well as heregulin ligands, in the fetal pancreas and in the IFNγ transgenic pancreas. The association of these molecules with endocrine cell and islet formation suggests that they play important roles in mediating new islet growth during pancreatic development, as well as during IFNγ-mediated pancreatic regeneration.

EXAMPLE 2

Expression of Msx-2 in the Regenerating and Developing Pancreas

Elevated expression of the homeobox-containing protein Msx-2 was observed in the pancreata of fetal mice as well as adult IFNγ mice, identifying this molecule as a novel marker associated with pancreatic development and regeneration as well. The identification of PDX-1 and Msx in the ducts of the IFNγ transgenic pancreas but not in ducts of the non-transgenic pancreas suggests that these molecules are associated with endocrine precursor cells in the ducts of the IFNγ transgenic mouse.

Transcription factors important for insulin gene expression are critical for the development of the pancreas during embryogenesis (see Sander and German (1997) *J Mol Med* 75 327–340). PDX-1 (also called IDX-1, IPF-1, or STF-1), a transcription factor that regulates insulin expression, is one important marker. Like PDX-1, Msx-2 is a homeobox-containing transcription factor. Msx-2 is part of a conserved family of transcription factors that play critical roles in tissue patterning and organogenesis during development (Davidson and Hill (1991), supra.) For example, the involvement of Msx-2 in bone and tooth development has been well-described. Notably, Msx-2 is expressed at a wide variety of sites in the developing embryo, suggesting its involvement in the generation of a number of organ systems. Nevertheless, no specific role is known for Msx-2 in pancreatic development.

Materials and Methods

Animal husbandry. Animals were maintained in a specific pathogen-free facility at The Scripps Research Institute according to the rules and regulations governed and enforced by the Institutional Animal Care and Use Committee. Animals were housed under a controlled 12-hour light/dark cycle and provided with food and water ad libitum. The embryos used in these studies did not carry the IFNγ transgene.

Transgenic mouse generation. Transgenic mice expressing IFNγ have been described previously (Sarvetnick et al. (1988) supra.) The IFNγ transgenic mice used in these studies were on the NOD background. IFNγ mice that have been backcrossed onto the NOD/Shi strain for more than ten generations have a very low incidence of diabetes, <20%, compared to NOD mice, which have an incidence of ~80% for females and ~25% for males.

Immunohistochemistry. Pancreata from test mice were fixed overnight in 10% neutral buffered formalin (3.6% formaldehyde) and embedded in paraffin. 5 m paraffin sections were either conventionally stained with hematoxylin and eosin (H&E) for histological evaluation or stained for the presence of insulin, PDX-1, or Msx using immunocytochemical techniques. Briefly, sections were deparaffinized and blocked with 2% normal goat serum before applying the primary antibodies for insulin (DAKO, Carpentaria, Calif.), Msx (BAbCO, Richmond, Calif.), or PDX-1 (a generous gift from Dr. Chris Wright, Vanderbilt University Medical School, Nashville, Tenn. and Dr. Helena Edlund, University of Umeå, Umeå, Sweden). Binding of the primary antibody was detected using the appropriate secondary antibody (Vector Laboratories, Burlingame, Calif.), and the horseradish peroxidase (HRP)-labeled avidin-biotin complex (ABC kit, Vector Laboratories). HRP was visualized using 3,3'-diaminobenzidine as a substrate. Gill's hematoxylin was used as a counterstain.

Immunoelectron Microscopy. Pancreatic tissue was fixed in 10% normal buffered formalin (3.6% formaldehyde) for 2 hours at 25° C. Fixed tissue was infused in 1 .5M sucrose-PBS for 0.5 hours with gentle inversion periodically. Infused tissue was then quick-frozen in liquid nitrogen, embedded in OCT and 2-methylbutane and sectioned 30–40 m thick. These sections were incubated in glycine-PBS to quench aldehyde for 0.5 hours, blocked in 10% normal goat serum for 0.5 hours, incubated for 1 hour each in PDX-1 (primary antibody) and an HRP-conjugated goat anti-rabbit secondary antibody before refixing in 1% glutaraldehyde-PBS for 0.25 hours and washing in PBS. The reaction product was visualized with diaminobenzidine (DAB) for 7 minutes and DAB+$H_2O_2$ for 4 minutes before treating with 1% $OsO_4$. Tissue was dehydrated in graded EtOH, cleared in propylene oxide and embedded in Spurr resin. Thin sections were viewed with a Hitachi HU 12A electron microscope.

Differential Gene Expression Analysis. The Atlas Mouse cDNA Expression Array I (Clontech, Palo Alto, Calif.) was used to screen the IFNγ NOD-SCID-regenerating pancreas for upregulation of mRNAs relative to the non-transgenic NOD-SCID pancreas. The analysis was carried out according to the manufacturer's recommendations. Msx-2 was one of nineteen transcripts found to be expressed in the regenerating pancreas but not in the non-transgenic pancreas.

Results

Figure 6:
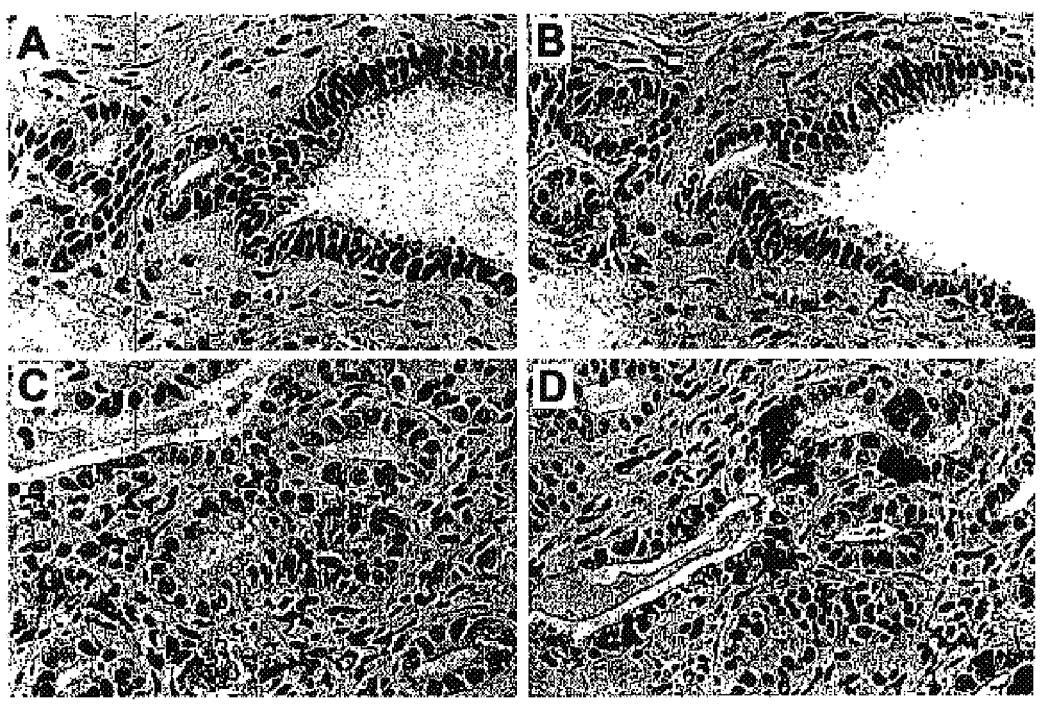
FIGS. 6A–D. Msx immunostaining in the IFNγ transgenic pancreas. Serial sections of the pancreas from an adult IFNγ transgenic mouse were stained with antibody to either PDX-1 (A), Msx (B, C), or insulin (D). Significant expression of Msx is seen, as well as PDX-1 in panels A and B (the arrows in panel B highlight Msx-positive cells in the duct wall). Msx-positive cells lacking insulin expression are indicated by arrows in panel C; insulin-positive cells lacking Msx expression are indicated by arrows in panel D. Panels C and D represent serial sections somewhat offset and at slightly different magnifications. Magnification A, B, D 40×; C 50×.

PDX-1 and Msx in the Fetal Pancreas. We first sought to characterize PDX-1, Msx-2, and insulin expression during fetal pancreatic development for comparison to that during regeneration, with the results summarized in Table 1. After staining of pancreata from E14.5 Balb/c embryos, PDX-1 reactivity was most notable in the cord region of expanding epithelial tissue from which the ducts and endocrine tissue develop, and was also observed in the acinar tissue, consistent with previous reports. Although less extensive than PDX-1 staining, Msx displayed considerable staining in the expanding epithelia of the developing pancreas where PDX-1 was also detected. Both nuclear and diffuse cytoplasmic staining were observed with this antibody as well, and faint nuclear staining in the acinar tissue was also detected (FIG. 6A). Finally, insulin-producing cells were also found in the region of expanding epithelia in the embryonic pancreas (FIG. 6B). Compared to PDX-1 and Msx staining, its expression was not as widespread within the cords, but rather was restricted more to the peri-epithelial region (FIG. 6 illustrates this point in a comparison of Msx and insulin staining patterns).

TABLE 1

Summary of PDX-1, Msx and Insulin Staining

|  |  | PDX-1 | MSX | Insulin |
|---|---|---|---|---|
| Fetal Balb/c | duct (cord) | +++ | + | +/− |
|  | peri-epithelial | +++ | ++ | ++ |
|  | acinar | ++ | +/− | − |
| Adult IFNγ transgenic | duct | +++ | ++ | + |
|  | acinar | − | − | − |
|  | islet | +++ | + | +++ |
| non-transgenic | duct | − | − | − |
|  | acinar | − | − | − |
|  | islet | +++ | + | +++ |

Plus signs refer to the extent of staining, from low (+/−_to extensive (+++). Peri-epithelial staining refers to staining abutting the ductal cord region.

Figure 7A:
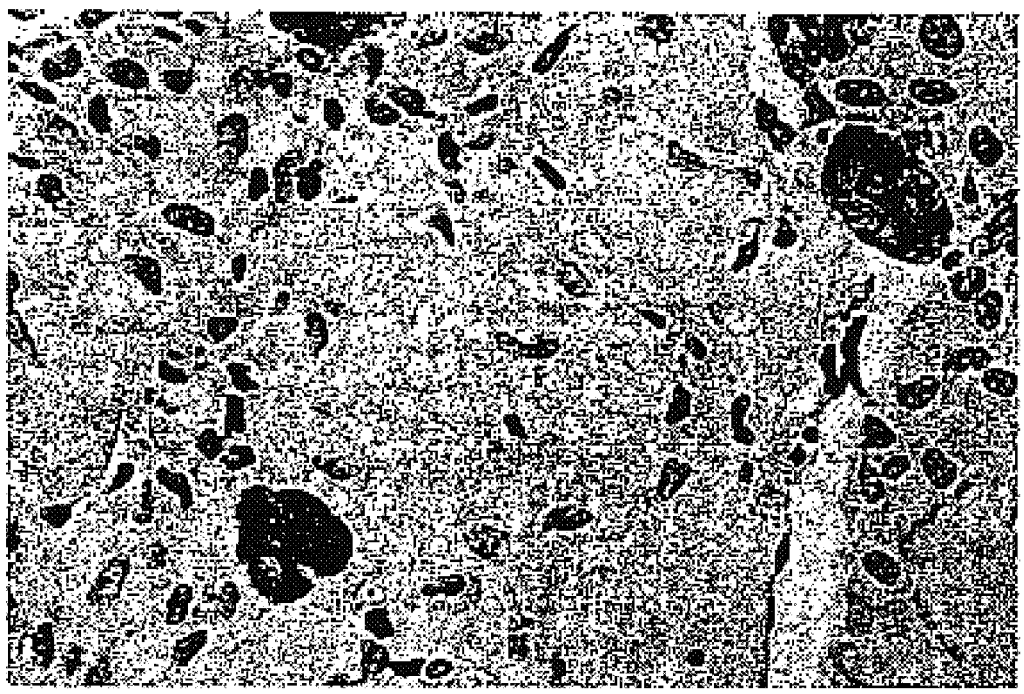
FIGS. 7A and 7B. Engraftment and differentiation of transplanted in vitro cultured pancreatic ductal "stem cells". Ductal cells were maintained in culture, and then implanted under the kidney capsule of an adult IFNγ transgenic. The sections were stained with antibody to insulin.
Figure 7B:
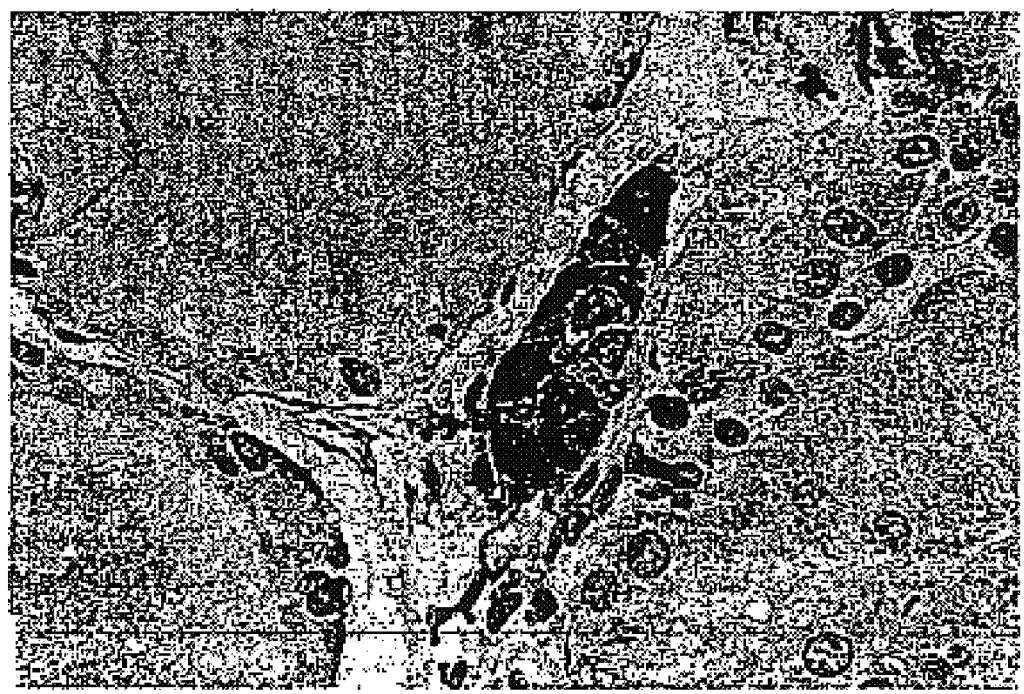

Msx expression in IFNg mice. Sections of regenerating pancreata from adult IFNg mice were screened for the presence of the Msx proteins by staining with a polyclonal antibody directed against the Msx homeodomain. The only antibody available for this purpose recognizes both the Msx-1 and Msx-2 proteins and probably Msx-3 as well. Our analyses demonstrated diffuse Msx staining throughout the islets of all mice assessed. In contrast, acinar tissue did not stain with the Msx antibody. Importantly, a significant portion of duct cells in the regenerating pancreas were positive for Msx expression (FIGS. 7B and 7C). We observed staining in the nucleus, as expected for members of this transcription factor family; however, cytoplasmic staining was also observed in many instances. The extent of staining varied among ducts; some ducts had many positive cells and other ducts had few, if any, Msx-positive cells. No Msx expression was evident in the ducts of non-transgenic control mice. Furthermore, Msx staining was less extensive than PDX-1 staining in the transgenic ducts, and comparison of serial section staining patterns suggested that Msx-expressing cells also expressed PDX-1 (FIGS. 7A and 7B). Subsequent analyses further suggested coincident staining between insulin and Msx in many instances.

Although the similarity in Msx and insulin expression patterns could reflect a basal level of cross-reactivity between the Msx antibodies and endocrine cells (supported by the diffuse islet staining we observe with the Msx antibody), we identified Msx-positive cells that did not stain for insulin in a number of ducts; insulin-positive cells lacking Msx expression were also observed (FIGS. 6A and 6B).

Based on PDX-1, Msx, and insulin staining patterns, at least four populations of ductal cells can be identified in the IFNγ transgenic pancreas: PDX-1$^+$ Msx$^-$ insulin$^-$ ductal cells; PDX-1$^+$ Msx$^+$ insulin$^-$ ductal cells; PDX-1$^+$ Msx$^+$ insulin$^+$ ductal cells; and PDX-1$^+$ Msx$^-$ insulin$^+$ ductal cells.

In this study, histological analyses were used to characterize the progenitor cells responsible for the ductal proliferation and islet regeneration. Defined markers associated with ducts during regeneration in the IFNg transgenic mouse include: PDX-1 and Msx-2. These results suggest that these proteins are associated with endocrine progenitor cells in the ducts of the IFNγ transgenic mouse.

The ductal epithelium has been designated as the site of exocrine and endocrine development in the pancreas. A specific pathway for islet development is thought to involve the derivation of endocrine cells from duct cells, which progress through a series of intermediate cell types. In promoting regeneration and new islet formation, it is believed that progenitor stem cells in the ducts of the IFNγ transgenic mouse recapitulate the early development of the pancreas. Parallels exist between normal ontogeny and IFNγ-mediated regeneration, and in both cases, endocrine gene expression is an early event. Individual endocrine cells are initially scattered in the duct wall; these cells subsequently migrate to form clusters, which develop into fully differentiated islets. Thus it was hypothesized that endocrine cell precursors would be abundant in the ducts of mice undergoing islet regeneration, as they are in the fetal pancreas.

Msx-2 is part of a conserved family of homeobox-containing transcription factors that regulate tissue growth and patterning during embryogenesis. Using the Atlas cDNA array to study differential gene expression patterns, we found that Msx-2 is expressed in the regenerating pancreas of the IFNγ transgenic mouse. We used immunohistochemistry to confirm these results and to follow expression of the Msx protein directly. These experiments utilized an antibody which detects both Msx-1 and Msx-2, preventing us from drawing conclusions regarding Msx-2 expression specifically from this staining alone. Despite this limitation, we detected significant expression of Msx in the pancreatic ducts of IFNγ transgenic mice. This is in contrast to the work of others as well as our own observations in non-transgenic mice demonstrating that the Msx proteins are not expressed in the normal adult mouse pancreas.

Strikingly, we also observed significant expression of Msx in the developing pancreas during embryogenesis. This expression was localized to the growing epithelia from which ducts and endocrine cells arise. Coupled with the fact that we did not observe enhanced Msx-1 expression in the transgenic pancreas using the Atlas cDNA array, these results support our identification of Msx-2 as a marker associated with endocrine progenitor cells both in the developing and regenerating pancreas. Furthermore, our staining demonstrated considerable cytoplasmic as well as nuclear localization of Msx. As a transcription factor, Msx is expected to be localized in the nucleus, although others have reported its presence as a diffuse cytoplasmic stain as well.

A number of studies indicate that Msx-2 can be induced through a signaling network involving members of the TGF beta superfamily, including BMP-4. TGFα, IL1β, and TNFα are elevated in the regenerating pancreas. Msx-2 is expressed at many sites during development, including the cranial neural crest, neural tube, tooth germs, eyes, ears, nose, limb buds, pituitary, and heart, and, in particular, Msx-2 expression appears to be associated with sites of epithelial-mesenchymal interactions. Msx proteins are also thought to be crucial to pattern formation during the development of diverse organs. A number of reports have also implicated Msx-2 in the apoptotic program during development. Although the expression of Msx-2 in the pancreas during development has not been reported previously, the evidence presented here suggests that Msx-2 plays a critical role in regulating the pancreatic developmental program as well.

The identification of markers associated with endocrine progenitor cells in the IFNγ transgenic pancreas is clearly of value, with regards to both defining these precursor cells and in an analysis of the regenerative process. In this study we have correlated the expression of two such molecules, PDX-1 and Msx-2, with the striking pancreatic regeneration exhibited by the IFNγ transgenic mouse. Each of these homeodomain proteins appears to play a critical role in organ formation during ontogeny, and each is expressed in the developing as well as the regenerating pancreas. While future studies will be aimed at defining the precise contributions of these proteins during pancreatic development and regeneration, their association with pancreatic progenitor cells will be valuable in the isolation and characterization of this critical cell type.

EXAMPLE 3

Engraftment and Differentiation of in Vitro Cultured Pancreatic Ductal Cells

Whole pancreata were harvested from IFNγ transgenic and non-transgenic mice. Ductal fragments were subsequently isolated and dispersed into cell suspensions. These ductal cell preparations were cultured for four months. A large portion (50%) of these cultured cells was found to express the ErbB3 receptor, while a separate population of smaller cells was found to be fibronectin positive, ErbB3 receptor negative. No endocrine cells were present in these long-term cultures. Cultured cells were then transplanted under the kidney capsule of recipient mice; each mouse received two hundred thousand cells. The transplanted cells were permitted to grow in vivo for three weeks, at which point the recipient mice were sacrificed. Isolated kidneys were prepared for immunohistochemical analysis. Staining for insulin expression revealed the presence of insulin-producing cells within the grafts (as shown in FIGS. 7A and 7B). These data indicate that cells purified and cultured from pancreatic ducts and engrafted into recipient mice can give rise to insulin-expressing cells at the graft site. Similar results were obtained with experiments to detect the presence of progenitors giving rise to glucagon producing alpha cells.

The purification of ErbB3-expressing cells from the cultured pancreatic duct preparations and their subsequent engraftment into recipient mice may significantly enhance the extent of insulin-producing cells generated within the graft.

All publications mentioned herein are incorporated herein by reference for the purpose of describing and disclosing, for example, the compounds and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method of identifying mammalian pancreatic islet progenitor cells, the method comprising:
   contacting a population of normal fetal or neonatal mammalian pancreatic cells with marker ErbB2 specific binding members comprising a detectable label ErbB2; and
   detecting those cells that bind to said ErbB2 specific binding members;
   wherein cells that bind to said ErbB2 specific binding members are identified as pancreatic islet progenitor cells.

2. The method of claim 1, wherein said pancreatic cells are human.

3. The method of claim 1, wherein said pancreatic cells are mouse.

4. The method of claim 1, wherein said marker ErbB2 specific binding member is an antibody.

5. The method of claim 1, wherein said detecting step comprises detection of said label by flow cytometry.

6. The method of claim 5, further comprising the step of:
   separating the cells in said population based on binding to said ErbB2 specific binding members to provide a purified population of pancreatic progenitor cells.

7. An isolated population of pancreatic islet progenitor cells, wherein said cells are derived from normal fetal or neonatal pancreatic ducts, and are characterized as expressing ErbB2.

8. The isolated cell population of claim 7, wherein said cells are human cells.

9. The isolated cell population of claim 7, wherein said cells are mouse cells.

10. An in vitro cell culture, comprising:
    a cell population according to claim 7; and
    cell culture medium.

11. A method of identifying mammalian pancreatic islet progenitor cells, the method comprising:
    contacting a population of normal fetal or neonatal mammalian pancreatic cells with ErbB3-specific binding members comprising a detectable label; and
    detecting those cells that bind to said ErbB3-specific binding members;
    wherein cells that bind to said ErbB3-specific binding members are identified as pancreatic islet progenitor cells.

12. The method of claim 11, wherein said cells are human cells.

13. The method of claim 11, wherein said cells are mouse cells.

14. The method of claim 11, wherein said ErbB3-specific binding member is an antibody.

15. The method of claim 11 wherein said detecting step comprises detection of said label by flow cytometry.

16. The method of claim 11, further comprising the step of:
    separating the cells in said population based on binding to said ErbB3-specific binding members to provide a purified population of pancreatic progenitor cells.

17. An isolated population of pancreatic islet progenitor cells, wherein said cells are derived from normal fetal or neonatal mammalian pancreatic cells, and are characterized as expressing ErbB3.

18. The isolated cell population of claim 17, wherein said pancreatic islet progenitor cells are progenitors for insulin producing beta cells.

19. The isolated cell population of claim 17, wherein said cells are further characterized as lacking detectable production of insulin.

20. A method of identifying mammalian pancreatic islet progenitor cells, the method comprising:
    contacting a population of normal fetal or neonatal mammalian pancreatic cells with ErbB4-specific binding members comprising a detectable label; and
    detecting those cells that bind to said ErbB4-specific binding members;
    wherein cells that bind to said ErbB4-specific binding members and that lack expression of glucagon or insulin are identified as pancreatic islet progenitor cells.

21. The method of claim 20, wherein said cells are human cells.

22. The method of claim 20, wherein said cells are mouse cells.

23. The method of claim 20, wherein said ErbB4-specific binding member is an antibody.

24. The method of claim 20, wherein said detecting step comprises detection of said label by flow cytometry.

25. The method of claim 20, further comprising the step of:

separating the cells in said population based on binding to said ErbB4-specific binding members to provide a purified population of pancreatic progenitor cells.

26. An isolated population of pancreatic islet progenitor cells, wherein said cells are derived from normal fetal or neonatal mammalian pancreatic cells, and are characterized as expressing ErbB4 and lacking detectable production of insulin or glucagon.

27. The isolated cell population of claim 17, wherein said pancreatic islet progenitor cells are progenitors for glucagon producing alpha cells.

* * * * *

UNITED STATES PATENT AND TRADEMARK OFFICE
CERTIFICATE OF CORRECTION

PATENT NO.    : 6,753,153 B2
DATED         : June 22, 2004
INVENTOR(S)   : Nora Sarvetnick et al.

It is certified that error appears in the above-identified patent and that said Letters Patent is hereby corrected as shown below:

Column 23,
Line 58, the word -- marker -- after the word "with" and before the word "ErbB2" should be removed.

Column 24,
Line 3, the word -- marker -- after the word "said" and before the word "ErbB2" should be removed.

Signed and Sealed this

Fourteenth Day of September, 2004

JON W. DUDAS
*Director of the United States Patent and Trademark Office*